US012582745B2

(12) United States Patent
Zeng et al.

(10) Patent No.: US 12,582,745 B2
(45) Date of Patent: Mar. 24, 2026

(54) ADHESIVE COMPOSITION FOR HARD TISSUE REPAIR

(71) Applicant: JIAXING JINGYIN BIOTECHNOLOGY CO., LTD, Jiaxing (CN)

(72) Inventors: Weiping Zeng, Beijing (CN); Xianghao Zhang, Beijing (CN); Tuanfeng Zhou, Beijing (CN); Yang Wang, Beijing (CN); Chenggang Duan, Beijing (CN)

(73) Assignee: JIAXING JINGYIN BIOTECHNOLOGY CO., LTD, Jiaxing (CN)

( * ) Notice: Subject to any disclaimer, the term of this patent is extended or adjusted under 35 U.S.C. 154(b) by 380 days.

(21) Appl. No.: 18/256,563

(22) PCT Filed: Mar. 5, 2021

(86) PCT No.: PCT/CN2021/079314

§ 371 (c)(1),
(2) Date: Jun. 8, 2023

(87) PCT Pub. No.: WO2022/121131

PCT Pub. Date: Jun. 16, 2022

(65) Prior Publication Data

US 2024/0016973 A1 Jan. 18, 2024

(30) Foreign Application Priority Data

Dec. 11, 2020 (CN) ......................... 202011433713.9

(51) Int. Cl.
*A61L 24/06* (2006.01)

(52) U.S. Cl.
CPC .................................... *A61L 24/06* (2013.01)

(58) Field of Classification Search
CPC ....................................................... A61L 24/06
See application file for complete search history.

(56) References Cited

U.S. PATENT DOCUMENTS

| | | | | |
|---|---|---|---|---|
| 5,866,632 A * | 2/1999 | Hashimoto | .............. | A61K 6/62 524/533 |
| 2008/0171841 A1 | 7/2008 | Zeng et al. | | |
| 2012/0219544 A1 | 8/2012 | Asada et al. | | |
| 2012/0225012 A1 | 9/2012 | Asada et al. | | |

FOREIGN PATENT DOCUMENTS

| | | | |
|---|---|---|---|
| CN | 1909870 | A | 2/2007 |
| CN | 102596269 | A | 7/2012 |
| CN | 105056291 | A | 11/2015 |
| JP | H05253284 | A | 10/1993 |
| JP | H0748219 | A | 2/1995 |
| JP | 2005-200342 | A | 7/2005 |
| JP | 3998737 | B2 | 10/2007 |
| JP | 2002-363022 | A | 12/2022 |

OTHER PUBLICATIONS

International Search Report in International Application No. PCT/CN2021/079314, dated Aug. 23, 2021.

* cited by examiner

*Primary Examiner* — Benjamin J Packard
(74) *Attorney, Agent, or Firm* — HAUPTMAN HAM, LLP

(57) ABSTRACT

An adhesive composition for hard tissue repair, comprising a polymerizable monomer (A), a polymer powder (B), and a polymerization initiator (C), wherein the polymerization initiator (C) is represented by the following general formula: [CH3(CH2)m-]2B—O(CH2)nCH3, and in the formula, m and n are each independently an integer from 1 to 4, and the relational expression that 2m+n<=10 is satisfied. The polymerization initiator cannot show coking or ignitability even when in contact with paper, a porous fiber, and the like in air, and is high in fluidity and easy to take a small and correct amount, so as to reduce adverse effects on a human body; and high polymerization activity can be given to a polymerizable composition, so that the polymerizable composition is cured within a short time, and the adhesive composition suitable for hard tissue repair is provided.

5 Claims, No Drawings

ADHESIVE COMPOSITION FOR HARD TISSUE REPAIR

TECHNICAL FIELD

The present invention relates to an adhesive composition for hard tissue repair and a polymerization initiator for said adhesive. More particularly, the present invention relates to an adhesive composition for hard tissue repair having high curability and adhesion properties and, to a polymerization initiator for the adhesive, which has improved safety against ignition when adhered to paper or the like.

TECHNICAL BACKGROUND

It is well known that the adhesion composition with trialkylboron as a polymerization initiator exhibits good adhesion to body hard tissue (see patent literature 1). Trialkylboron is an extremely unstable substance in air, and reacts vigorously with oxygen to ignite spontaneously when exposed to air, and thus not suitable for general clinical use. Therefore, various techniques have been developed for improving the safety of trialkylboron.

Patent literature 2 discloses a method for improving the safety against easy ignition by adding hydrophobic and viscous substances such as vaseline, paraffin wax and organosilicon, i.e., silicone oil, to trialkylboron or derivatives thereof, adding adsorbents such as silicic acid and alumina, if desired, and making into paste.

Patent literature 3 discloses a dental or surgical adhesive using partially oxidized trialkylboron as a polymerization initiator, a product obtained by reacting trialkylboron with 0.3 to 0.9 moles of oxygen. Although, the invention of patent literature 3 proposes a polymerization initiator that minimizes the activity of trialkylboron to improve the safety against ignition, it is difficult to obtain a reactant of a certain composition since this polymerization initiator results from a liquid-gas reaction of trialkylboron with oxygen, thereby leading to the instability of the curing rate of the adhesive using it as the initiator and inhibiting ignition incompletely.

Patent literature 4 discloses a polymerization initiator obtained in a homogeneous mixture by adding organic oligomers or organic polymers such as silicone oil, wax, oligoester, oligoamide, and the like to an organoboron compound. The addition of large amounts of additives tends to cause a decrease in polymerization initiation activity, and an increase in viscosity affects the correct measuring.

Patent literature 5, 6 propose a method for improving the safety against ignition by adding polymer powder of alkyl (meth)acrylate to tributylboron or partially oxidized tributylboron to prepare a paste initiator. The addition of large amounts of additives tends to cause a reduction in polymerization initiation activity, and the paste initiator is difficult to correct measuring.

With respect to the ignition of trialkylboron, Patent literature 7 proposes a mixture based on oxyalkylalkylboron obtained by reacting trialkylboron with an alkyl alcohol, or further adding a polar organic compound or an inert diluent material to the mixture to improve the safety of the polymerization initiator, but it is not sufficient.

Patent literature 8 proposes a method for improving the safety by adding an aprotic solvent or further adding an inert liquid or a solid organic oligomer or polymer to tributylboron or partially oxidized tributylboron. However, the addition of large amounts of additives tends to result in reduced activity of the polymerization initiator and sometimes leads to an increase in the viscosity of the initiator composition due to the addition of the organic oligomer or polymer, which causes difficulty in accurately measuring the amount.

Patent literature 9 proposes the addition of specific amounts of alkanes and alcohols to tributylboron or partially oxidized tributylboron to inhibit ignition and improve the safety. However, the effect of paraffins remaining in the adhesive that cannot be absorbed and decomposed by the human body on the health of the human body is unknown when the initiator is used, and the addition of large amounts of additives results in a reduction in the activity of the polymerization initiator.

PATENT LITERATURE LIST

Patent literature 1: JPS42-14318
Patent literature 2: JPS48-11892
Patent literature 3: JPS49-5143
Patent literature 4: JPS58-084803
Patent literature 5: JPH3-264509
Patent literature 6: CN1642933A
Patent literature 7: JPH5-253284
Patent literature 8: JPH9-110913
Patent literature 9: CN1909870A To sum up, there is still a room for the improvement in the initiator or initiator composition of the adhesive composition for hard tissue repair of the prior art in terms of use safety, use convenience, and biosafety.

SUMMARY OF THE INVENTION

It is an object of the present invention to provide a polymerization initiator which does not cause coking or exhibits ignition even w % ben contacting paper, porous fibers or the like in the air, has high flowability, can be easily and accurately measured in a small amount, reduces adverse effects on the human body, and can impart high polymerization activity to the polymerizable composition so as to cure the polymerizable composition in a short time, thereby an adhesive composition suitable for hard tissue repair is provided.

In order to achieve the above object, an organoboron compound with a high purity and a specific structure is used to inhibit ignition and maintain its high flowability and high polymerization activity, and thus, the present invention was accomplished. The technical embodiments adopted by the invention are as follows:

An adhesive composition for hard tissue repair comprising:

a polymerizable monomer (A), a polymer powder (B), and a polymerization initiator (C), wherein the polymerization initiator (C) is represented by the following general formula (1):

[CH3(CH2)m-]2B—O(CH2)nCH3 (1)

in the general formula (1), m and n are each independently an integer from 1 to 4 and satisfy the equation: 2m+n<=10;

wherein the polymerizable monomer (A) is a (meth) acrylate ester or a combination of a (meth)acrylate ester and a polymerizable monomer containing an acidic group;

wherein the polymer powder (B) is at least one polymer selected from homopolymer of alkyl (meth)acrylate, copolymer between alkyl (meth)acrylates, copolymer of alkyl (meth)acrylate with other polymerizable monomer, copolymer of alkyl (meth)acrylate with alkylene di(meth)acrylate, and copolymer of alkyl (meth)acrylate with diene monomer;

wherein the polymerization initiator (C) is an alkoxydialkylboron having a purity of 97% or more;

wherein the polymerization initiator (C) is an alkoxydialkylboron having a purity of 98% or more;

wherein the polymerization initiator (C) is butoxydibutylboron;

the adhesive composition for hard tissue repair comprises 20-70 parts by weight of the polymerizable monomer (A), 20-70 parts by weight of the polymer powder (B), and 1-20 parts by weight of the polymerization initiator (C), wherein the total amount of the polymerizable monomer (A), the polymer powder (B), and the polymerization initiator (C) is 1(0) parts by weight;

wherein the composition further comprises 20-150 parts by weight of a filler (D) based on 100 parts by weight of the total amount of the polymerizable monomer (A), the polymer powder (B), and the polymerization initiator (C). The filler (D) is an inorganic filler, an organic filler, or an organic-inorganic composite filler, which is insoluble or non-swellable in the polymerizable monomer (A).

The present invention provides a polymerization initiator which does not cause coking or exhibits ignition even when contacting paper, porous fibers or the like in the air, has high flowability, can be easily and accurately measured in a small amount, reduces adverse effects on the human body, and can impart high polymerization activity to the polymerizable composition so that the polymerizable composition is cured within a short time, thereby an adhesive suitable for hard tissue repair is provided.

Based on the common knowledge, reaction activity of alkylboron with oxygen, i.e., ignitability is believed to be proportional to its polymerization initiation property. However, surprisingly, the alkoxydialkylboron of the present invention having lower ignition than trialkylboron and partially oxidized trialkylboron has equivalently high polymerization initiation property. The reason for this is not clear, but as one of the reasons, it is speculated that the reaction between alkoxydialkylboron of the present invention and oxygen is relatively mild compared to trialkylboron and partially oxidized trialkylboron, and the proportion of the primary free radicals generated that are consumed by the mutual reaction without being used for the polymerization initiation is relatively small, so the generated free radicals can be effectively used for polymerization initiation.

As shown in example 1 and comparative example 1 and comparative example 2 in table 1, when the partially oxidized tributylboron and the mixture of butoxydibutylboron are contacted with the filter paper, the filter paper can be coked and even ignited, while the high-purity butoxydibutylboron of the present invention does not cause coking or ignition of the filter paper when contacting the filter paper, at the same time, has polymerization activity equivalent to those of partially oxidized tributylboron and the mixture of butoxydibutylboron.

DETAILED DESCRIPTION OF THE PRESENT INVENTION

[Polymerizable Monomer (A)]

The polymerizable monomer (A) used in the present invention is not particularly limited as long as it can be polymerized by the polymerization initiator (C) described hereinafter. With respect to the polymerizable monomer (A), both monofunctional monomers and polyfunctional monomers may be used depending on the purpose of use.

As the polymerizable monomer (A), (meth)acrylate ester monomers and other vinyl compounds may be used for example. Considering less irritation to human body, (meth) acrylate ester monomers are preferred. In the present invention, "(meth)acrylate ester" is the generic name of acrylate and methacrylate. In addition, the monomer having an acidic group is generally excellent in adhesion to hard tissue and metal material such as titanium for hard tissue repair, and therefore, the polymerizable monomer (A) can also contain an appropriate amount of the monomer having an acidic group to improve the adhesion to hard tissue and repairing material.

As specific examples of a monofunctional (meth)acrylate ester monomer without an acidic group, alkyl (meth)acrylate such as methyl (meth)acrylate, ethyl (meth)acrylate, propyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth) acrylate, isobornyl (meth)acrylate; hydroxyalkyl (meth) acrylate such as 2-hydroxyethyl (meth)acrylate, 2-hydroxypropyl (meth)acrylate, 3-hydroxypropyl (meth)acrylate, 4-hydroxybutyl (meth)acrylate, 5-hydroxyamyl (meth)acrylate, 6-hydroxyhexyl (meth)acrylate, 1,2-dihydroxypropyl mono(meth)acrylate, 1,3-dihydroxypropyl mono(meth) acrylate, erythritol mono(meth)acrylate; polyethylene glycol mono(meth)acrylate such as diethylene glycol mono(meth) acrylate, triethylene glycol mono(meth)acrylate, polyethylene glycol mono(meth)acrylate, and polydipropylene glycol mono(meth)acrylate; (poly) glycol monoalkyl ether (meth) acrylate such as ethylene glycol monomethyl ether (meth) acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate, polypropylene glycol monoalkyl ether (meth)acrylate; fluoroalkyl (meth) acrylate such as perfluorooctyl (meth)acrylate, hexafluorobutyl (meth)acrylate; silane compounds having (meth) acryloyloxyalkyl such as gamma-(meth) acryloyloxypropyltrimethoxysilane, gamma-(meth) acryloyloxypropyltris(trimethylsiloxy) silane, and the like; (meth)acrylate having heterocycle such as tetrafurfuryl (meth)acrylate can be mentioned.

As specific examples of a polyfunctional (meth)acrylate ester monomer without an acidic group, poly(meth)acrylate of alkane polyol such as ethylene glycol di(meth)acrylate, propylene glycol di(meth)acrylate, butanediol di(meth)acrylate, neopentyl glycol di(meth)acrylate, hexanediol di(meth) acrylate, dihydroxypropyl di(meth)acrylate, trimethylolpropane tri(meth)acrylate, pentaerythritol tetra(meth)acrylate; polyoxyalkane polyol poly(meth)acrylates such as diethylene glycol di(meth)acrylate, triethylene glycol di(meth) acrylate, polyethylene glycol di(meth)acrylate, dipropylene glycol di(meth)acrylate, polypropylene glycol di(meth)acrylate, dibutylene glycol di(meth)acrylate, dipentaerythritol hexa(meth)acrylate can be mentioned;

Alicyclic or aromatic di(meth)acrylate represented by the following general formula (2)

(2)

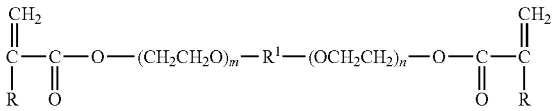

wherein R is hydrogen atom or methyl, m and n are the same or different and are numbers from 0 to 10, wherein $R^1$ is

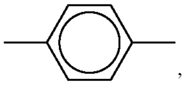
,
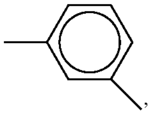
,
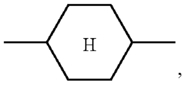
,
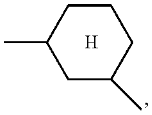
,
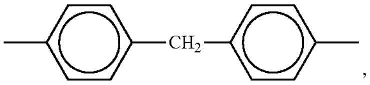
,
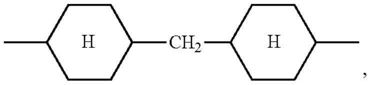
,
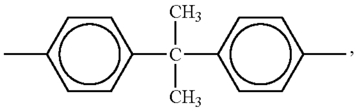
,
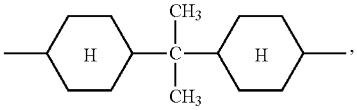
,
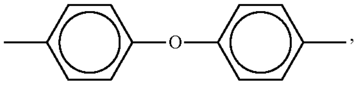
,
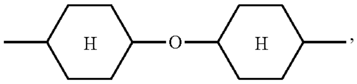
,
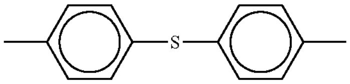
or
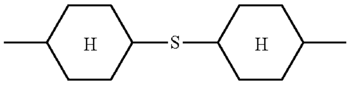

and an aliphatic or aromatic di(meth)acrylate having a hydroxyl group in the molecule represented by the following general formula (3):

(3)

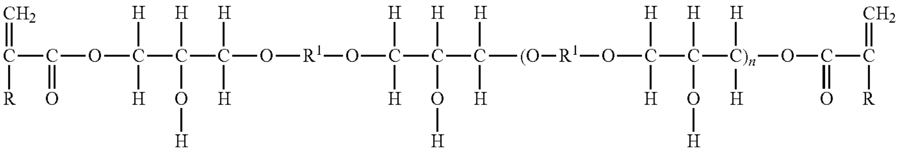

wherein R is hydrogen atom or methyl m is a number from 0 to 10, $R^1$ is

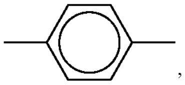
,
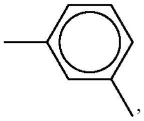
,
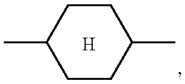
,
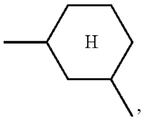
,
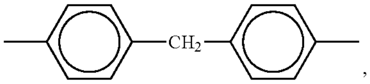
,
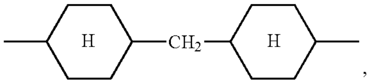
,
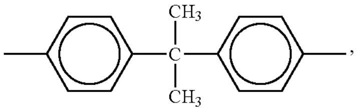
,
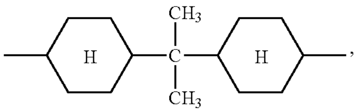
,
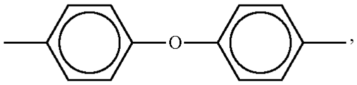
,
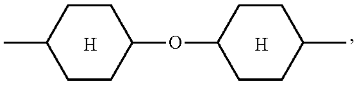
,
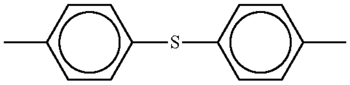
or
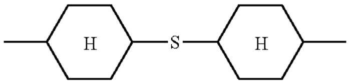

and a polyfunctional (meth)acrylate or the like having a urethane bond in the molecule represented by the following general formula (4);

(4)

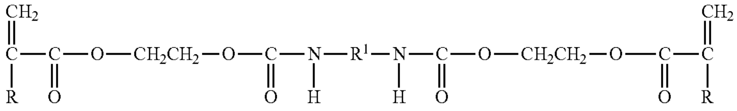

wherein R is hydrogen atom or methyl, $R^1$ is

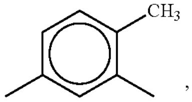

,

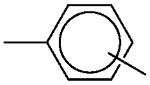

,

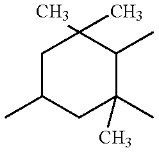

,

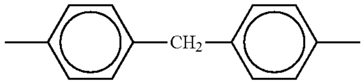

,

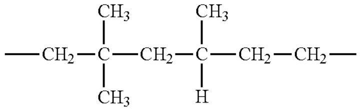

,

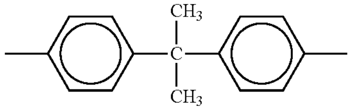

or

-continued

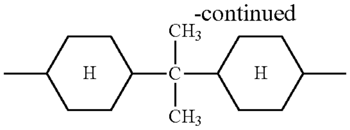

wherein, as the monofunctional (meth)acrylate, it is particularly preferred to use alkyl (meth)acrylate such as methyl (meth)acrylate and ethyl (meth)acrylate;

hydroxyl-containing (meth)acrylate such as 2-hydroxyethyl (meth)acrylate, 1,3-dihydroxypropyl mono(meth) acrylate, erythritol mono(meth)acrylate; (meth)acrylate having ethylene glycol chain in the molecule such as triethylene glycol monomethyl ether (meth)acrylate, triethylene glycol mono(meth)acrylate, etc.

Furthermore, as the polyfunctional (meth)acrylate, di(meth)acrylate having an ethylene glycol chain in the molecule, such as triethylene glycol di(meth)acrylate, polyethylene glycol di(meth)acrylate, or the like, dihydroxypropyl di(meth)acrylate is particularly preferred;

Compounds represented by the following formula (2)-a:

(2)-a

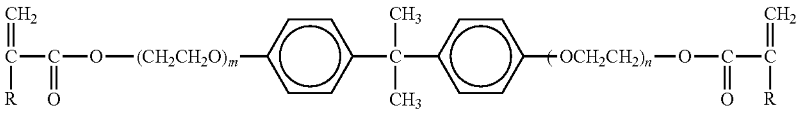

wherein R, m and n have the same definitions as in formula (2);

Compound represented by the following formula (3)-a:

(3)-a

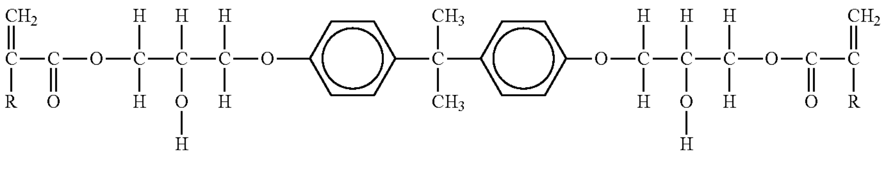

wherein R has the same definition as in formula (3);

Compounds represented by the following formula (4)-a, and the like:

(4)-a

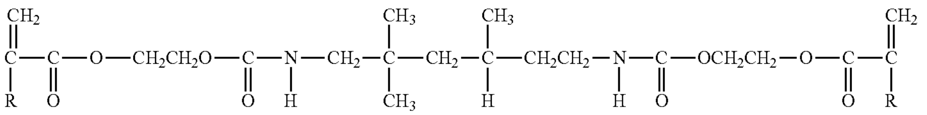

wherein R has the same definition as in formula (4). These can be used alone or in combination of two or more.

Specific examples of monomers having an acidic group are as follows:

The monomer having a carboxylic acid group or anhydride group such as (meth)acrylic acid and its anhydride, 1,4-di(meth)acryloyloxyethyl pyromellitic acid, 6-(meth) acryloyloxyethyl naphthalene 1,2,6-tricarboxylic acid, N-(meth)acryloyl p-aminobenzoic acid. N-(meth)acryloyl anthranilic acid, N-(meth)acryloyl m-aminobenzoic acid, N-(meth)acryloyl-5-aminosalicylic acid, N-(meth)acryloyl-4-aminosalicylic acid, 4-(meth)acryloyloxyethyl trimellitic acid and its anhydride, 4-(meth)acryloyloxybutyl trimellitic acid and its anhydride, 4-(meth)acryloyloxyhexyl trimellitic acid and its anhydride, 4-(meth)acryloyloxydecyl trimellitic acid and its anhydride, 2-(meth)acryloyloxybenzoic acid, 3-(meth)acryloyloxybenzoic acid, 4-(meth)acryloyloxybenzoic acid, beta-(meth)acryloyloxyethyl succinate, beta-(meth)acryloyloxyethyl maleate, beta-(meth)acryloyloxyethyl phthalate, 11-(meth)acryloyloxy-1,1-undecanedicarboxylic acid and p-vinylbenzoic acid; the monomer having an phosphoric acid group such as (2-(meth)acryloyloxyethyl) phosphoric acid, (2-(meth)acryloyloxyethylphenyl) phosphoric acid, 10-(meth)acryloyloxydecyl phosphoric acid, and the like; the monomer having an sulfonic acid group such as p-styrenesulfonic acid, 2-acrylamido-2-methylpropanesulfonic acid and the like can be mentioned, preferably 4-methacryloyloxyethyl trimellitic acid and its anhydride. These acidic monomers can be used alone or in combination.

In the polymerizable monomer (A), preferably 80% by weight or more is a monofunctional (meth)acrylate ester monomer, more preferably 90% by weight or more is a monofunctional (meth)acrylate ester monomer, and more preferably 95% by weight or more is a monofunctional (meth)acrylate ester monomer. If the monomer (A) comprises the monomer comprising an acidic group, the amount of the monomer comprising an acidic group is preferably 1 to 20% by weight, based on 100% by weight of the total monomer (A).

The polymerizable monomer (A) is present in an amount of preferably 20 to 70 parts by weight, more preferably 30 to 65 parts by weight, and more preferably 35 to 60 parts by weight based on 100 parts by weight of the total amount of the polymerizable monomer (A), the polymer powder (B) and the polymerization initiator (C). The lower limits of the above ranges are meaningful in terms of operability, penetration of the composition into the hard tissue etc. The upper limits are meaningful in terms of curing rate, early adhesion strength, mechanical properties, etc.

[Polymer Powder (B)]

The type of polymer powder (B) used in the present invention is not particularly limited, the polymer powder which is soluble or swellable in the polymerizable monomer (A) of the present invention can be used. As the polymer powder (B), (meth)acrylate ester polymer and other vinyl polymer can be used, wherein (meth)acrylate ester polymer is preferred. For example, homopolymer of alkyl (meth) acrylate, copolymer of between alkyl (meth)acrylates, copolymer of alkyl (meth)acrylate with other polymerizable monomer, copolymer of alkyl (meth)acrylate with alkylene di(meth)acrylate, and copolymer of alkyl (meth)acrylate with diene monomer can be mentioned. These can be used alone or in combination of two or more.

Examples of (meth)acrylate ester polymers can include non-crosslinked polymer such as poly methyl (meth)acrylate, poly ethyl (meth)acrylate, copolymer of methyl (meth) acrylate and ethyl (meth)acrylate, copolymer of methyl (meth)acrylate and butyl (meth)acrylate, copolymer of methyl (meth)acrylate and styrene; crosslinked polymer such as copolymer of methyl (meth)acrylate and ethylene glycol di(meth)acrylate, copolymer of methyl (meth)acrylate and triethylene glycol di(meth)acrylate, copolymer of methyl (meth)acrylate and butadiene monomer.

The polymer powder (B) is present in an amount of preferably 20 to 70 parts by weight, more preferably 30 to 65 parts by weight, and more preferably 35 to 60 parts by weight, based on 100 parts by weight of the total amount of the polymerizable monomer (A), the polymer powder (B) and the polymerization initiator (C).

[Polymerization Initiator (C)]

The polymerization initiator (C) of the present invention is an alkoxydialkylboron represented by the following general formula (1)

$$[CH3(CH2)m\text{-}]2B\text{—}O(CH2)nCH3 \qquad (1)$$

in the general formula (1), m and n are each independently an integer from 1 to 4 and satisfy the equation: 2m+n<=10;

As specific example of an alkoxydialkylboron, examples can include ethoxydiethylboron, ethoxydipropylboron, ethoxydibutylboron, ethoxydiamylboron, propoxydiethylboron, propoxydipropylboron, propoxydibutylboron, propoxydiamylboron, butoxydiethylboron, butoxydipropylboron, butoxydibutylboron, preferably ethoxydibutylboron, propoxydibutylboron, butoxydibutylboron, more preferably propoxydibutylboron, butoxydibutylboron, especially butoxydibutylboron. These can be used alone or in combination of two or more.

The purity of alkoxydialkylboron used in the present invention is preferably 97% or more, more preferably 98% or more, and particularly preferably 98.5% or more. Surprisingly, when the purity of the alkoxydialkylboron used in the present invention is above a certain degree, its ignition is significantly inhibited, but still retains the equivalent polymerization activity.

For the preparation of alkoxy dialkylboron, it can be obtained by reacting trialkylboron having a corresponding number m in the general formula (1) with an alcohol having corresponding number n. Since the reaction must be carried out under an oxygen-insulated condition and is relatively sensitive to reaction temperature, generally a mixture (primary product) containing target alkoxydialkylboron as main component is obtained. The high-purity alkoxydialkylboron of the present invention is obtained by reduced pressure distillation fractionation of said primary product.

For the preparation of alkoxydialkylboron, it can also be obtained by oxidation reaction of trialkylboron with an oxidant such as oxygen. When oxygen is used as the oxidant, since the reaction of trialkylboron with oxygen is liquid-gas heterogeneous reaction, reaction conditions such as gas feeding rate and stirring rate must be strictly controlled. Reaction of trialkylboron with oxygen typically results in a mixture containing the target alkoxydialkylboron as the main component. High purity alkoxydialkylboron of the present invention can be obtained by reduced pressure distillation fractionation of the mixture.

Preferably, the polymerization initiator (C) is present in an amount of 1 to 20 parts by weight, more preferably 2 to 15 parts by weight, and more preferably 3 to 10 parts by weight, based on 100 parts by weight of the total amount of the polymerizable monomer (A), the polymer powder (B), and the polymerization initiator (C).

Without affecting the performance of the polymerization initiator of the present invention, 0.01 to 5 parts by weight of an alcohol with a boiling point in the range of 60 to 120° C., preferably 0.05 to 4 parts by weight, more preferably 0.1 to 3 parts by weight, can be added, based on 100 parts by weight of the organoboron compound (C) if desired.

[Filler (D)]

The type of filler (D) used in the present invention is not particularly limited and inorganic fillers, organic fillers and organic-inorganic composite fillers all can be used as long as they are insoluble or non-swellable in the polymerizable monomer (A) of the present invention.

Examples of the inorganic filler useful as the filler (D) of the present invention include metal oxide powders such as zirconia, bismuth oxide, titania, zinc oxide, and alumina particles; metal salt powders such as calcium carbonate, bismuth carbonate, calcium phosphate, zirconium phosphate, and barium sulfate; hydroxyapatite, carbonate apatite, anhydrous calcium hydrogen phosphate; glass fillers such as silica glass, aluminum-containing glass, barium-containing glass, strontium-containing glass and zirconium silicate glass; fillers for slowly releasing silver; fillers for slowly release fluorine. These inorganic fillers can be used alone or in combination.

In order to obtain a strong adhesion between the inorganic filler and the resin, it is preferable to use an inorganic filler which has undergone a surface treatment such as silane treatment or polymer coating.

In the composition of the present invention, the amount of filler (D) is preferably 20 to 150 parts by weight, more preferably 30 to 120 parts by weight, especially 35 to 100 parts by weight, and most preferably 40 to 80 parts by weight, based on 100 parts by weight of the total amount of the polymerizable monomer (A), the polymer powder (B) and the polymerization initiator (C).

[Other Components]

The adhesive composition for hard tissue repair of the present invention may include, as desired, a polymerization inhibitor. As a specific example of the polymerization inhibitor, hydroquinone compounds such as hydroquinone and dibutylhydroquinone; phenols such as hydroquinone monomethyl ether, 2,6-di-tert-butylphenol, 2,6-di-tert-butyl p-cresol, catechol, pyrogallol, benzoquinone, 2-hydroxybenzoquinone, p-methoxyphenol, tert-butyl catechol, butylated hydroxyanisole, butylated hydroxytoluene and tert-butylhydroquinone. The polymerization inhibitor can be used alone or in combination of two or more, preferably, the mixture of hydroquinone monomethyl ether and 2,6-di-tert-butyl p-cresol. Generally, the polymerization inhibitor is added to the polymerizable monomer (A). The polymerization inhibitor is added in an amount of from 10 to 1000 ppm, more preferably from 20 to 500 ppm, more preferably from 25 to 200 ppm, based on the polymerizable monomer (A).

The composition for hard tissue repair of the present invention may contain an ultraviolet absorber such as benzotriazole or the like, if desired. The amount of the ultraviolet absorber is added in an amount of preferably 5 to 500 ppm, more preferably 10 to 200 ppm, based on the polymerizable monomer (A).

As other components, antiinfective agent, antibacterial agent, antiviral agent, hemostatic agent, platelet activator, bone formation factor, bone growth factor, synthetic peptide with hemostatic effect, and other pharmaceutical or therapeutic components can also be included.

As an example of other component, a colorant can also be included to visually clarify the distinction between the composition and the surrounding hard tissue.

The adhesive composition for hard tissue repair of the present invention is prepared by mixing the polymerizable monomer (A), the polymer powder (B), the polymerization initiator (C) and if desired other components, or prepared by mixing the polymerizable monomer (A), the polymer powder (B), the polymerization initiator (C), the filler (D), and if desired other components. There is no particular restriction on the mixing order when mixing the components. It is preferable to first mix the polymerizable monomer (A) with the polymerization initiator (C) and then mix the polymer powder (B) or the polymer powder (B) and the filler (D) in view of the more excellent stability of the resulting composition for hard tissue repair.

With respect to the adhesive composition for hard tissue repair of the present invention, the polymerizable monomer (A), the polymer powder (B), the polymerization initiator (C), and if desired other components, alternatively, the polymerizable monomer (A), the polymer powder (B), the polymerization initiator (C), the filler (D), and if desired all other components, are divided into three or more parts in any combination and stored in three or more members, respectively, and the components are mixed immediately before use to obtain the composition for hard tissue repairs.

EXAMPLES

The present invention is described in further detail below on the basis of the examples, but is not limited by these examples.

The abbreviations used hereinafter refer to the following compounds, respectively MMA: methyl methacrylate 4-META: 4-methacryloyloxyethyl trimellitic anhydride p-(MMA/BuMA): copolymer of methyl methacrylate and butyl methacrylate (particle size 68 μm, MMA content is about 25% by weight)

Example 1

(1) Preparation of the Polymerization Initiator 182 g tri-n-butylboron was injected into the reactor under nitrogen atmosphere, and the temperature of the reactant was kept not higher than 80° C. 74 g anhydrous n-butanol was gradually dropped under stirring, the reactant was heated in nearly circulating state under stirring. After 24 hours of reaction, the heating was stopped to obtain a mixture of butoxydibutylboron.

The above mixture of butoxydibutylboron was distilled under reduced pressure under nitrogen atmosphere, a fraction under 92-94° C./8 mm Hg was collected. The purity was 97.6% by gas chromatography via relative area analysis, which was the target polymerization initiator and was stored in a nitrogen box before use.

(2) Ignition Test 0.5 ml of the polymerization initiator composition was dropped onto a filter paper (whatman, No. 3) at 23° C.±2° C., the filter paper was stood to observe whether the filter paper was coked and ignited.

(3) Polymerization Initiator Measuring Test:

The dropping state of the polymerization initiator composition was judged with naked eyes by dropping it from the syringe. Good measurability: drop by drop, no drawing/bubble mixing; Poor measurability: continuous dripping of the liquid droplets or drawing/bubble mixing, or non-dripping.

(4) Polymerization Activity Test (Determination of Cure Time):

1) In a room at 25±2° C., 0.18 g of monomer (composition: MMA/4-META=95/5, weight ratio), 2 drops (about 0.015 g) of the polymerization initiator were dropped into a glass mixing dish, and 0.16 g of polymethacrylic acid (number average molecular weight: 400000, average particle size: about 25 μm) was further added, slightly mixed for 10 seconds to make resin mud;
2) A thin layer of vaseline was coated on a glass plate, a Teflon ring (outer diameter 13 mm, inner diameter 10 mm, thickness 5 mm) also coated with the thin layer of vaseline was placed on the glass plate, and the resin mud was poured on the glass plate;
3) Within 30 seconds after the beginning of mixing, the glass plate containing the resin mud was transferred into a thermostat at 37±2° C. and 100% humidity. A probe was allowed to quietly fall on the surface of the test body to check whether the needle mark was formed. The time from the beginning of mixing to the time when no needle mark was formed on the test body was taken as the curing time.

The results were shown in table 1:

The evaluation was conducted the same as in example 1, except that the partially oxidized tributylboron above was used as the polymerization initiator (C). The results were shown in table 1.

Comparative Examples 3-4

The evaluation was conducted the same as in example 1, except that the polymerization initiator composition consisted of partially oxidized tributylboron and additives in the amounts shown in table 1 were used as the polymerization initiator (C). The results were shown in table 1.

Comparative Example 5

For the preparation of the polymerization initiator (C), n-butanol in example 1 was replaced with n-hexanol to react with tributylboron. A fraction under 126-128° C./10 mm Hg was obtained by distillation under reduced pressure and used as the initiator and was stored in a nitrogen box before use. Except that, the evaluation was conducted the same as in example 1. The results were shown in Table 1.

TABLE 1

Initiator for ignition safety, measurability, polymerization activity and other performances

| | Initiator/initiator composition (weight ratio) | Character | Measurability | Safety against ignition Coked | Safety against ignition ignited | Polymerization activity (curing time) |
|---|---|---|---|---|---|---|
| Example 1 | Butoxydibutylboron (purity 97.6%) | colorless liquid | good | – | – | 8 min 10 s |
| Comparative example 1 | Mixture of butoxydibutylboron | colorless liquid | good | + | – | 8 min 0 s |
| Comparative example 2 | Partially oxidized tributylboron(TBB•O) | colorless liquid | good | + | + | 7 min 40 s |
| Comparative example 3 | TBB•O/acetone/P-MMA/BuMA = 100/56/30 | viscous liquid | bad | – | – | 9 min 0 s |
| Comparative example 4 | TBB•O/n-hexane/ethanol = 100/20/3 | colorless liquid | good | – | – | 8 min 30 s |
| Comparative example 5 | hexyloxydibutylboron(purity 97.3%) | colorless liquid | good | – | – | more than 20 min |

In table 1, description of the symbols in the safety test sample for ignition:
Not coked/not ignited: –
Coked/ignited: +

Comparative Example 1

The evaluation was conducted the same as in example 1, except that the mixture of butoxydibutylboron of example 1 above was used as the polymerization initiator (C). The results were shown in table 1.

Comparative Example 2

Reference 1. Preparation of partially oxidized tributylboron 182 g of tri-n-butylboron was injected into the reactor under nitrogen atmosphere; the temperature of the reactant was kept not higher than 40'C, the dry air was slowly blown on the surface of the reaction liquid while stirring; air corresponding to 0.5 molar equivalent of oxygen was blown in over about 6 hours to obtain a mixture of the partially oxidized tributylboron (TBB.O), which was stored in a nitrogen box prior to use.

Example 2 (Adhesion Strength to Hard Tissue)

(1) Under the condition of water injection, the lip part of the ox anterior tooth was ground with coarse emery paper to expose the flat enamel surface, and then further polished with 600 #emery paper to form the adhesion surface. After dying the adhesion surface, it was treated with 35 wt. % phosphoric acid etching solution for 10 sec, washed with water for 10 sec, blow dried for 15 sec. Then, a hollow cellophane adhesive tape with a diameter of 4 mm was pasted on the adhesion surface to define the adhesion area.
(2) The resin mud was prepared at the same ratio as in the polymerization activity test of Example 1 (4).
(3) The resin mud was coated on the adhesion surface prepared by (1), and the acrylic rod was bonded to obtain a sample for adhesion test.

The sample for the adhesion test was placed at room temperature for 30 minutes, further impregnated in distilled water at 37° C. for 24 hours. The adhesion strength of the acrylic rod to the dental enamel was tested via a tensile test. The adhesion strength was the average of the values measured five times on the test samples. The adhesion strength was 10.2 MPa.

As described above, the present invention provides a polymerization initiator which does not cause coking or exhibits ignition even when contacting paper, porous fibers or the like in the air, has high flowability, can be easily and accurately measured in a small amount, reduces adverse effects on the human body, and can impart high polymerization activity to the polymerizable composition, thereby an adhesive suitable for hard tissue repair is provided.

The above description is merely illustrative of the preferred embodiments of the invention and is not intended to limit the invention, it is intended that any modifications, equivalents, substitutions, and modifications made within the spirit and principles of the invention are embraced within the scope of the invention.

The invention claimed is:

1. An adhesive composition for hard tissue repair, consisting of a polymerizable monomer (A), a polymer powder (B), and a polymerization initiator (C), wherein the polymerization initiator (C) is a butoxydibutylboron having a purity of 97% or more;

wherein the polymerizable monomer (A) is a (meth) acrylate ester or a combination of a (meth)acrylate ester and a polymerizable monomer containing an acidic group;

wherein the polymer powder (B) is at least one polymer selected from homopolymer of alkyl (meth)acrylate, copolymer between alkyl (meth)acrylates, copolymer of alkyl (meth)acrylate with other polymerizable monomer, copolymer of alkyl (meth)acrylate with alkylene di(meth)acrylate, and copolymer of alkyl (meth)acrylate with diene monomer.

2. The adhesive composition for hard tissue repair according to claim 1, wherein the polymerization initiator (C) is a butoxydibutylboron having a purity of 98% or more.

3. The adhesive composition for hard tissue repair according to claim 1, wherein the adhesive composition for hard tissue repair comprises 20-70 parts by weight of the polymerizable monomer (A), 20-70 parts by weight of the polymer powder (B), and 1-20 parts by weight of the polymerization initiator (C), wherein the total amount of the polymerizable monomer (A), the polymer powder (B), and the polymerization initiator (C) is 100 parts by weight.

4. The adhesive composition for hard tissue repair according to claim 1, wherein the adhesive composition for hard tissue repair further comprises 20-150 parts by weight of a filler (D) based on 100 parts by weight of the total amount of the polymerizable monomer (A), the polymer powder (B), and the polymerization initiator (C), wherein the filler (D) is an inorganic filler, an organic filler, or an organic-inorganic composite filler, which is insoluble or non-swellable in the polymerizable monomer (A).

5. The adhesive composition for hard tissue repair according to claim 1, wherein the polymerization initiator (C) is a butoxydibutylboron having a purity of 97.6%.

* * * * *